United States Patent
Boesten et al.

(10) Patent No.: US 7,713,724 B2
(45) Date of Patent: May 11, 2010

(54) HYDANTOIN RACEMASE

(75) Inventors: Wilhelmus Hubertus Joseph Boesten, Sittard (NL); Joannes Gerardus Theodorus Kierkels, Sittard (NL); Friso Bernard Jan Assema, Geleen (NL); Luis Miguel Ruiz Pérez, Granada (ES); Dolores González Pacanowska, Granada (ES); Jesús González López, Granada (ES); Santiago De La Escalera Hueso, Mojaca (ES)

(73) Assignee: DSM IP Assets B.V., Heerlen (NL)

( * ) Notice: Subject to any disclaimer, the term of this patent is extended or adjusted under 35 U.S.C. 154(b) by 1576 days.

(21) Appl. No.: 10/515,800

(22) PCT Filed: May 23, 2003

(86) PCT No.: PCT/NL03/00386

§ 371 (c)(1),
(2), (4) Date: Jul. 15, 2005

(87) PCT Pub. No.: WO03/010050

PCT Pub. Date: Dec. 4, 2003

(65) Prior Publication Data

US 2006/0035321 A1    Feb. 16, 2006

(30) Foreign Application Priority Data

May 23, 2002    (NL) .................................... 1020663

(51) Int. Cl.
C07H 21/04 (2006.01)
C12P 13/04 (2006.01)
C12N 9/90 (2006.01)

(52) U.S. Cl. .................. 435/233; 435/69.1; 435/106; 435/320.1; 435/325; 536/23.2

(58) Field of Classification Search ........................ None
See application file for complete search history.

(56) References Cited

U.S. PATENT DOCUMENTS 6,815,195 B2 * 11/2004 Suzuki et al. ............... 435/233

FOREIGN PATENT DOCUMENTS

| EP | 1 188 826 | 3/2002 |
|---|---|---|
| JP | 04271784 | 9/1992 |
| WO | WO-01/23535 | 4/1991 |
| WO | WO-01/23582 | 4/2001 |

OTHER PUBLICATIONS

Wood et al. (Science 2001, vol. 294, 2317-2323).*
Capela et al., PNAS USA (2001) 98:9877-9882.
Database EMBL 'Online,' Dec. 18, 2001, Database accession No. AE009399 XP002226620.
Database SWISSPROT 'Online', Dec. 12, 2001, Database accession No. Q92ML1 XP002226619.
Durham et al., Biochemical and Biophysical Research Communications (1995) 216:1095-1100.
Gentz et al., PNAS USA (1989) 86:821-824.
Hartley et al., Applied Microbiology and Biotechnology (2001) 57:43-49.
International Search Report for PCT/NL03/00386, mailed on Sep. 17, 2003, 3 pages.
Las Heras-Vazquez et al., Biochem. Biophys. Res. Commun. (2003) 303:541-547.
Makrides, Microbiological Reviews (1996) 512-538.
Watabe et al., J. Bact. (1992) 174:3461-3466.
Watabe et al., J. Bact. (1992) 174:7989-7995.
Wiese et al., J. of Biotechnology (2000) 80:217-230.
Wood et al., Science (2001) 294:2317-2323.

* cited by examiner

*Primary Examiner*—Rebecca E. Prouty
*Assistant Examiner*—Md. Younus Meah
(74) *Attorney, Agent, or Firm*—Nixon & Vanderhye P.C.

(57) ABSTRACT

The invention relates to isolated polypeptides with hydantoin recemase activity, that do not suffer from substrate inhibition. Such polypeptides arc for instance isolated polypeptides with at least 87% identity with SEQ ID: NO. 2 or SEQ ED: NO. 4. The invention also relates to nucleic acid sequences encoding these polypeptides. The invention also relates to processes for the racemisation of enantiomerically enriched hydantoin compounds and to processes for the preparation of enantiomarically enriched I)-or I-α amino acids.

15 Claims, 1 Drawing Sheet

Figure 1: Relative initial activity of hydantoin racemases from A. radiobacter, Pseudomonas strain NS671 and Arthrobacter aurescens DSM 3747 versus initial L-5-methylmercaptoethylhydantoin concentration
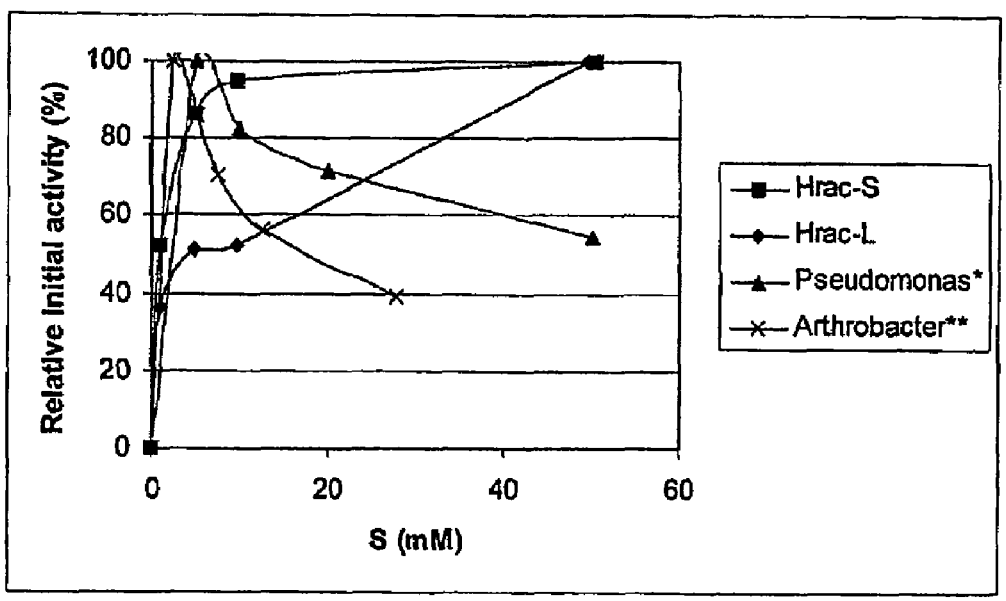
\* Plot drawn from data from Watabe et al. (1992)
\*\* Plot drawn from data from Wiese et al. (2000)

SEQUENCE LISTING

<160> NUMBER OF SEQ ID NOS: 7

<210> SEQ ID NO 1
<211> LENGTH: 717
<212> TYPE: DNA
<213> ORGANISM: Agrobacterium radiobacter

<400> SEQUENCE: 1

```
atgcatattc gtctgatcaa cccgaactca accgcctcga tgacggcgca ggcactggac      60
agcgccctgc gtgtcaaaca ggcgcacacg acgatctcag cgacaaatcc cctcgatacg     120
cctgtcagca tcgaaggcgg ggccgatgag gcgctggctg ttccgggcat gctggaggaa     180
atccgcaagg gtgagcgtct gggcgtcgat gcctatgtca ttgcctgctt tgacgatccc     240
ggcctgcacg ctgcccggga agtggcgcgc ggtcccgtca tcggtatctg ccaggccggc     300
attcaggtgg ccatgaccat cagccgccgt ttttccatca tcacgacgct gccgcgctcc     360
attccgatta tcgaagacct cgtcgacaat tatggcgctc agcgtcactg ccgccgggtc     420
cgcgccatca atctgccggt gctcggtctc gaggaggatc cgcatgccgc agaggcgatg     480
ctgatccgcg aaatcgaagc ggcaaagaaa gaggatgcgg cagaagccat catccttggc     540
tgcgccggca tgtcggcact gtgcgacagg ctgcgcgagg caacgggcgt ccccgtgatc     600
gatggcgtca ccgccgccgt caagctggcg gaggcactgg tgggcgctgg atacagcacc     660
tccaaggtca atgcctatga ttatccgcgc atcaaggaaa ccaagctcgt cgcctga       717
```

<210> SEQ ID NO 2
<211> LENGTH: 238
<212> TYPE: PRT
<213> ORGANISM: Agrobacterium radiobacter

<400> SEQUENCE: 2

```
Met His Ile Arg Leu Ile Asn Pro Asn Ser Thr Ala Ser Met Thr Ala
1               5                  10                  15

Gln Ala Leu Asp Ser Ala Leu Arg Val Lys Gln Ala His Thr Thr Ile
            20                  25                  30

Ser Ala Thr Asn Pro Leu Asp Thr Pro Val Ser Ile Glu Gly Gly Ala
        35                  40                  45

Asp Glu Ala Leu Ala Val Pro Gly Met Leu Glu Glu Ile Arg Lys Gly
    50                  55                  60

Glu Arg Leu Gly Val Asp Ala Tyr Val Ile Ala Cys Phe Asp Asp Pro
65                  70                  75                  80

Gly Leu His Ala Ala Arg Glu Val Ala Arg Gly Pro Val Ile Gly Ile
                85                  90                  95

Cys Gln Ala Gly Ile Gln Val Ala Met Thr Ile Ser Arg Arg Phe Ser
            100                 105                 110

Ile Ile Thr Thr Leu Pro Arg Ser Ile Pro Ile Ile Glu Asp Leu Val
        115                 120                 125

Asp Asn Tyr Gly Ala Gln Arg His Cys Arg Arg Val Arg Ala Ile Asn
    130                 135                 140

Leu Pro Val Leu Gly Leu Glu Glu Asp Pro His Ala Ala Glu Ala Met
145                 150                 155                 160

Leu Ile Arg Glu Ile Glu Ala Ala Lys Lys Glu Asp Ala Ala Glu Ala
                165                 170                 175

Ile Ile Leu Gly Cys Ala Gly Met Ser Ala Leu Cys Asp Arg Leu Arg
            180                 185                 190
```

```
Glu Ala Thr Gly Val Pro Val Ile Asp Gly Val Thr Ala Ala Val Lys
        195                 200                 205

Leu Ala Glu Ala Leu Val Gly Ala Gly Tyr Ser Thr Ser Lys Val Asn
        210                 215                 220

Ala Tyr Asp Tyr Pro Arg Ile Lys Glu Thr Lys Leu Val Ala
225                 230                 235

<210> SEQ ID NO 3
<211> LENGTH: 750
<212> TYPE: DNA
<213> ORGANISM: Agrobacterium radiobacter

<400> SEQUENCE: 3
atggcaaatg agcgtcctga aaggcgagcc cgaatgcata ttcgtctgat caacccgaac      60
tcaaccgcct cgatgacggc gcaggcactg acagcgccc tgcgtgtcaa acaggcgcac     120
acgacgatct cagcgacaaa tcccctcgat acgcctgtca gcatcgaagg cggggccgat     180
gaggcgctgg ctgttccggg catgctggag gaaatccgca agggtgagcg tctgggcgtc     240
gatgcctatg tcattgcctg ctttgacgat cccggcctgc acgctgcccg ggaagtggcg     300
cgcggtcccg tcatcggtat ctgccaggcc ggcattcagg tggccatgac catcagccgc     360
cgttttccca tcatcacgac gctgccgcgc tccattccga ttatcgaaga cctcgtcgac     420
aattatggcg ctcagcgtca ctgccgccgg gtccgcgcca tcaatctgcc ggtgctcggt     480
ctcgaggagg atccgcatgc cgcagaggcg atgctgatcc gcgaaatcga agcggcaaag     540
aaagaggatg cggcagaagc catcatcctt ggctgcgccg gcatgtcggc actgtgcgac     600
aggctgcgcg aggcaacggg cgtcccgtg atcgatggcg tcaccgccgc cgtcaagctg     660
gcggaggcac tggtgggcgc tggatacagc acctccaagg tcaatgccta tgattatccg     720
cgcatcaagg aaaccaagct cgtcgcctga                                      750

<210> SEQ ID NO 4
<211> LENGTH: 249
<212> TYPE: PRT
<213> ORGANISM: Agrobacterium radiobacter

<400> SEQUENCE: 4

Met Ala Asn Glu Arg Pro Glu Arg Arg Ala Arg Met His Ile Arg Leu
1               5                   10                  15

Ile Asn Pro Asn Ser Thr Ala Ser Met Thr Ala Gln Ala Leu Asp Ser
            20                  25                  30

Ala Leu Arg Val Lys Gln Ala His Thr Thr Ile Ser Ala Thr Asn Pro
        35                  40                  45

Leu Asp Thr Pro Val Ser Ile Glu Gly Gly Ala Asp Glu Ala Leu Ala
    50                  55                  60

Val Pro Gly Met Leu Glu Glu Ile Arg Lys Gly Glu Arg Leu Gly Val
65                  70                  75                  80

Asp Ala Tyr Val Ile Ala Cys Phe Asp Asp Pro Gly Leu His Ala Ala
                85                  90                  95

Arg Glu Val Ala Arg Gly Pro Val Ile Gly Ile Cys Gln Ala Gly Ile
            100                 105                 110

Gln Val Ala Met Thr Ile Ser Arg Arg Phe Ser Ile Ile Thr Thr Leu
        115                 120                 125

Pro Arg Ser Ile Pro Ile Ile Glu Asp Leu Val Asp Asn Tyr Gly Ala
    130                 135                 140
```

-continued

```
Gln Arg His Cys Arg Arg Val Arg Ala Ile Asn Leu Pro Val Leu Gly
145                 150                 155                 160

Leu Glu Glu Asp Pro His Ala Ala Glu Ala Met Leu Ile Arg Glu Ile
            165                 170                 175

Glu Ala Ala Lys Lys Glu Asp Ala Ala Glu Ala Ile Ile Leu Gly Cys
        180                 185                 190

Ala Gly Met Ser Ala Leu Cys Asp Arg Leu Arg Glu Ala Thr Gly Val
        195                 200                 205

Pro Val Ile Asp Gly Val Thr Ala Ala Val Lys Leu Ala Glu Ala Leu
        210                 215                 220

Val Gly Ala Gly Tyr Ser Thr Ser Lys Val Asn Ala Tyr Asp Tyr Pro
225                 230                 235                 240

Arg Ile Lys Glu Thr Lys Leu Val Ala
                245

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: primers

<400> SEQUENCE: 5
caccatgcat attcgtctga tcaacccg                                      28

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primers

<400> SEQUENCE: 6
tcaggcgacg agcttggttt c                                             21

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: primers

<400> SEQUENCE: 7
caccatggca aatgagcgtc ctgaaag                                       27
```

HYDANTOIN RACEMASE

CROSS-REFERENCE TO RELATED APPLICATION

This application is the national phase of PCT application PCT/NL03/00386 having an international filing date of 23 May 2003, which claims priority from European application 1020663 filed 23 May 2002. The contents of these documents are expressly incorporated herein by reference for all purposes.

The invention relates to isolated polypeptides with hydantoin racemase activity. In addition, the invention relates to the use of these polypeptides.

Polypeptides with hydantoin racemase activity, also called hydantoin racemases, are known in the art. They have been found in a variety of organisms, for instance, WO 01/23582 describes a hydantoin racemase from *Arthrobacter aurescens* (DSM.3747), and JP 04271784 describes a hydantoin racemase from *Pseudomonas* NS 671 (Watabe et al., J. Bact. 174; 3461–66 (1992)). Hydantoin racemases have also been described in *Sinorhizobium meliloti* (acc. Nr. CAC 47181, Capela et al., PNAS 98:9877–9882 (2001)), in *Microbacterium liquefaciens* (acc nr CAD 32593, EP 1.188.826), and in *Agrobacterium tumefaciens* strain C58 (acc. nrs. AAL 45498, AAK 88746 and AAK 90298, Las Heras-Vazquez et al., Biochem Biophys Res Commun 303:541–547 (2003), Wood et al., Science 2001, 294: 2317–23 and Hinkle et al., NCBI database, Complete Genome Sequence of *Agrobacterium tumefaciens* C58 (Rhizobium radiobacter C58), the Causative Agent of Crown Gall Disease in Plants. Direct Submission, Submitted 14 Aug. 2001).

In the framework of the invention, hydantoin racemase activity is understood to mean the ability to catalyze the racemization of substituted D or L hydantoins.

A drawback of the known hydantoin racemases is that they exhibit substrate inhibition, in particular towards L-5-methylmercaptoethylhydantoin. Wiese et al., for instance, describe the occurrence of substrate inhibition of the hydantoin racemase from *Arthrobacter aurescens* DSM 3747 at an L-5-methylmercaptoethylhydantoin concentration from 5 mM (J. Biotechn. 80; 217–230 (2000)). Also, the hydantoin racemase from *Pseudomonas* NS671 displayed substrate inhibition at similar concentrations (Watabe et al., J. Bact. 174; 3461–66 (1992)). As a consequence of this property, the enzyme can only be efficiently employed at low substrate concentrations.

It would be desirable to have a hydantoin racemase that would not suffer from the phenomenon of substrate inhibition since this would allow the racemisation of substituted D or L-hydantoin at higher substrate concentrations. This would effectively contribute to cost reduction in the production of intermediate and end products.

It is therefore an aim of the invention to provide hydantoin racemases that do not exhibit substrate inhibition.

Surprisingly, hydantoin racemases have been found that do not exhibit substrate inhibition. The object of the invention is therefore achieved by the provision of hydantoin racemases obtainable from *Agrobacterium radiobacter* or functional equivalents thereof. SEQ ID: NO. 2 and SEQ ID: NO. 4 give amino acid sequences of hydantoin racemases from *Agrobacterium radiobacter*. SEQ ID: NO. 4 has 11 additional amino acids at the N terminus when compared to SEQ ID: NO. 2. SEQ ID: NO. 1 gives the nucleic acid sequence from *Agrobacterium radiobacter* encoding the amino acid sequence shown in SEQ ID: NO. 2, whereas SEQ ID: No. 3 gives the nucleic acid sequence from *Agrobacterium radiobacter* encoding the amino acid sequence shown in SEQ ID: NO. 4.

In the framework of the invention, substrate inhibition is understood to mean a decrease in initial activity upon an increase in substrate concentration.

Within the scope of the present invention, functional equivalents of hydantoin racemases obtainable from *Agrobacterium radiobacter* are herein defined as polypeptides having hydantoin racemase activity that do not suffer from substrate inhibition by L-5-methylmercaptoethylhydantoin. Particularly useful examples of such functional equivalents are polypeptides which have at least 87%, more preferably at least 90% such as at least 93%, 95%, 97% 98% or 99% identity with SEQ ID: NO. 2 or with SEQ ID: NO.4. Hydantoin racemases obtainable from *Agrobacterium radiobacter* and functional equivalents thereof are herein collectively referred to as hydantoin racemases according to the invention or as polypeptides according to the invention.

The polypeptides with hydantoin racemase activity according to the invention have at least 87% Identity with SEQ ID: NO. 2 or SEQ ID: NO.4, preferably at least 90% identity with SEQ ID: NO. 2 or SEQ ID: NO. 4, more preferably at least 95%, in particular at least 97%, more in particular at least 98%, even more in particular at least 99%, most in particular at least 99.5% identity with SEQ ID: NO.2 or SEQ ID: NO. 4.

In the framework of the invention, the percentage identity between two amino acid sequences is determined with the aid of the blast pairwise alignment algorithm (NCBI) with an identity table and the following alignment parameters: mismatch=−3, penalty=−3, gap extend=1, match bonus=1, Gap x−droff=50, expect =10, wordsize=3.

In another embodiment the invention relates to isolated polypeptides with hydantoin racemase activity that do not suffer from substrate inhibition and which are encoded by nucleic acid sequences that hybridize under high stringency conditions, preferably under very high stringency conditions, with the nucleic acid sequence shown in SEQ ID: NO. 1 or SEQ ID: NO. 3 or the complements thereof.

Hybridization experiments can be performed using different methods, which are known in the art. General guidelines for the choice to be made between the various methods are for instance given in chapter 9 of Sambrook, J., Fritsh, E. F., Maniatis, T. Molecular Cloning: A Laboratory Manual, 2nd, ed., Cold Spring Harbor Laboratory, Cold Spring Harbor Laboratory Press, Cold Spring Harbor, N.Y., 1989.

The stringency of the hybridization conditions is understood to be the conditions under which the hybridization, consisting of the actual hybridization and washing steps, is carried out. Washing steps are used, for instance, to remove nucleic acids which do not hybridize with the target nucleic acid, which is for instance immobilized on a nitrocellulose filter. The stringency of the hybridization conditions can for instance be changed by changing the salt concentration in the wash liquor and/or the temperature at which the washing step is carried out (washing temperature). The stringency of the hybridization is for instance Increased by lowering the salt concentration in the wash liquor or by raising the washing temperature. In the framework of the invention hybridization is carried out in 6× sodium chloride/sodium citrate (SSC) at a temperature of about 45° C. for about 12 hours. Examples of hybridization conditions are two successive washing steps of 30 minutes each in 1×SSC, 0.1% SDS at 60° C. (high stringency hybridization conditions) or at 65° (very high stringency hybridization conditions).

In yet another embodiment the invention relates to isolated polypeptides with hydantoin racemase activity that do not suffer from substrate Inhibition and which exhibit immunological crossreactivity with antibodies against at least a part of the amino acid sequence of SEQ ID: NO. 2 or SEQ ID: NO. 4.

The immunological cross-reactivity can be demonstrated through the use of an antibody preparation against, or reactive with, at least one epitope of the isolated polypeptide with hydantoin racemase activity according to the invention. The antibody preparation, which may be monoclonal as well as polyclonal, can be produced using methods known in the art. The immunological cross-reactivity can also be demonstrated using methods known in the art. The production of an antibody and the demonstration of immunological cross-reactivity are for instance described in Hudson et al., Practical Immunology, Third Edition (1989), Blackwell Scientific Publications.

The invention also relates to fusion proteins obtainable by expression of a nucleic acid sequence encoding at least part of a polypeptide according to the invention which is operationally linked to one (or more) nucleic acid sequence(s) encoding a marker polypeptide. 'Operationally linked' Is understood to mean that the two nucleic acid sequences are linked in such a way that, when expressed, the polypeptide according to the invention is produced with the marker polypeptide(s) at its N- or C-terminus or at both terminus. The marker polypeptide can be used for many purposes; it can for instance be used to enhance the stability or the solubility of the fusion protein, as a secretion signal (a signal which directs the fusion protein to a particular compartment in the cell) or to facilitate the purification of fusion proteins. An example of a marker polypeptide used to facilitate the purification of fusion proteins is the hexahistidine peptide. The purification of a fusion protein with a hexahistidine label is described, for instance, in Gentz et al., (1989) Proc. Natl. Acad. Sci. USA, vol. 86, pp. 821–824. A fusion protein with a hexahistidine label can for instance be produced in a pQE vector (Qiagen, Inc.) according to the supplier's protocol.

The invention also comprises mutants of polypeptides with hydantoin racemase activity that have one or more mutations as compared to the naturally occurring amino acid sequence. Methods for making mutations are known to the person skilled in the art, examples being random mutagenesis (for instance with the aid of PCR or by means of UV irradiation), site directed PCR, etc, The invention also relates to nucleic acid sequences encoding polypeptides with hydantoin racemase activity according to the invention.

The nucleic acid sequence encoding a polypeptide according to the invention can be cloned into a suitable vector and after introduction into a suitable host cell, the nucleic acid sequence can be expressed so as to produce a polypeptide according to the invention. Cloning and expression of a nucleic acid sequence are standard techniques known in the art which are described for instance in Sambrook, J., Fritsh, E. F. and Maniatis, T. Molecular Cloning, A Laboratory Manual, 2nd ed., Cold Spring Harbor Laboratory, Cold Spring Harbor Laboratory Press, Cold Spring Harbor, N.Y., 1989.

A polypeptide according to the invention can also be produced by Integrating the nucleic acid sequence encoding this polypeptide into the genome of a host cell and by (over) expressing it. Integration of the nucleic acid sequence and (over)expression of this sequence can be effected using methods known to the person skilled in the art. It is also possible to over-express a polypeptide according to the invention in the microorganism in which it occurs naturally, for instance by placing a suitable promoter in front of the nucleic acid sequence according to the invention in the genome of the microorganism, by integrating one or more copies of a nucleic acid sequence according to the invention into the genome of the microorganism, or by overexpressing the nucleic acid sequence according to the invention in a suitable vector in its natural host.

The invention therefore also relates to a vector comprising a nucleic acid sequence according to the invention. The invention also relates to a host cell containing a nucleic acid sequence encoding a polypeptide according to the invention. Preferably the invention relates to a host cell containing a vector with a nucleic acid sequence according to the invention. The invention also relates to the over-expression of a nucleic acid sequence according to the invention.

Examples of vectors which are suitable for expressing a nucleic acid sequence according to the invention, are the vectors normally used for cloning and expression. These vectors are known to the average person skilled in the art. Examples of suitable vectors for expression in *Eschedchia coli* are given, for instance, in Table 1 in Makrides, S. C., Microbiological reviews, (1996), 512–538. The vector preferably possesses a cloning site being under the control of an inducible promoter. Examples of inducible promoters are: the lac promoter, the araBAD promoter, the T7 promoter, the trc promoter, the tac promoter and the trp promoter. Suitable host cells are the host cells normally used for cloning and expression and are known to the average person skilled in the art. Examples of suitable *E. coli* host cell strains are: TOP10F', TOP10, DH10B, DH5α, HB101, W3110, BL21(DE3) and BL21(DE3)pLysS, BL21Star(DE3).

The choice of a vector sometimes depends on the choice of a host cell (and the other way round); if, for instance, a vector with the araBAD promoter is used, then preferably an *E. coli* host cell strain is used which is not capable of degrading the arabinose inducer (*E. coli ara* host cell).

Nucleic acid sequences encoding a polypeptide according to the invention can be found in other organisms using standard molecular biological techniques and the sequence information given in the present document. For instance, the use of the entire sequence, or part of it, of the nucleic acid sequence described in SEQ ID: NO. 1 or SEQ ID: NO. 3 as a hybridization probe enables Isolation of nucleic acid sequences which encode a polypeptide according to the invention (for instance as described in Sambrook, J., Fritsch, E. F. and Maniatis, T. Molecular cloning: A Laboratory Manual, 2nd, ed., Cold Spring Harbor Laboratory, Cold Spring Harbor Laboratory Press, Cold Spring Harbor, N.Y., 1989).

A nucleic acid sequence which partly or wholly comprises SEQ ID: NO. 1 or SEQ ID: NO. 3 can also be found by means of the polymerase chain reaction (PCR) by using (synthetic) oligonucleotide primers which are based on the sequence information in SEQ ID: NO. 1, SEQ ID: NO. 2, SEQ ID: NO. 3 and/or SEQ ID: NO. 4.

A nucleic acid sequence according to the invention can be amplified using, for instance, cDNA, mRNA, genomic DNA as a template and the appropriate oligonucleotide primers, by means of standard PCR amplification techniques. The nucleic acid sequence thus amplified can be cloned into a suitable vector and can be characterized by DNA sequence analysis.

It is also possible to prepare oligonucleotides corresponding to or capable of hybridization with nucleic acid sequences according to the invention using standard synthesis techniques, for instance by using an automated DNA synthesizer.

The nucleic acid sequences according to the invention can, after isolation, be cloned Into a suitable vector and expressed in a suitable host cell, using methods known in the art, for production of a polypeptide according to the invention.

In case it needs to be confirmed that a cloned sequence indeed encodes a protein according to the invention, i.e. a hydantoin racemase that does not suffer from substrate inhibition, the procedure as outlined in example 3 may be followed.

Since it has now been established herein that hydantoin racemases exist that do no suffer from substrate inhibition, racemisation of D- or L-hydantoin may henceforth be performed at higher substrate concentrations. In one embodiment, the invention therefore relates to a process for the racemisation of an enantiomerically enriched hydantoin compound comprising the step of contacting said enantiomerically enriched hydantoin compound with a polypeptide having hydantoin racemase activity wherein the polypeptide having hydantoin racemase does not suffer from substrate inhibition. Such a process is hereinafter referred to as a process according to the invention.

In a preferred embodiment a hydantoin racemase according to the invention is used in a process according to the invention, more preferably a hydantoin racemase obtainable from *Agrobacterium radiobacter* is used in a process according to the invention, even more preferably a hydantoin racemase according to SEQ ID NO: 2 or SEQ ID NO: 4 is used in a process according to the invention.

Examples of D- or L-hydantoins which may be racemized by hydantion racemases according to the invention are: D- or L-hydantions of formula 1,

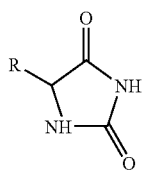

(1)

wherein R represents an amino acid rest group, for instance an optionally substituted (hetero)alkyl group with for instance 1–20 C-atoms or an optionally substituted (hetero)aryl group with for instance 1–20 C-atoms. Examples of substituents on the (hetero)aryl group or on the (hetero)alkyl group are: hydroxyl, alkoxy, mercapto, thioalkyl, alkyl, carboxyl, amino, nitro, halogens, carbamoyl, nitrile and acyl. Examples of R groups are: methyl, i-propyl, i-butyl, 2-methylthioethylene, 4-aminobutylene, hydroxymethylene, methoxymethylene, carboxymethylene, carboxyethylene, phenyl, p-hydroxyphenyl, m-hydroxyphenyl, o-hydroxyphenyl, p-chlorophenyl, m-chlorophenyl, 2,4-dichlorophenyl, p-methoxyphenyl, benzyl, p-hydroxybenzyl, 3,4-dihydroxybenzyl, 3,4-dimethoxybenzyl, benzyloxymethylene, 3,4-methylene dioxybenzyl, indolylmethylene.

The racemization of D- or L-hydantoin in a process according to the invention can be integrated into another process as well as take place externally. Integrated into a process is understood to mean that a D- (or L-) hydantoin is racemized and that L- (or D-) hydantoin of the resulting racemate is immediately converted further in situ, so that in fact racemization of D- (or L-) hydantoin takes place continuously. Externally is understood to mean that D- (or L-) hydantoin is racemized in a separate reaction step.

The Invention accordingly relates to a process for the preparation of enantiomerically enriched α-amino acids in the presence of 1) a hydantoin racemase that does not suffer from substrate inhibition
2) a hydantoinase and/or
3) an enantioselective carbamoylase.

The advantage of the use of hydantoin racemases in such processes is that it allows a faster and/or higher conversion of the substituted hydantoin into the corresponding α-amino acid in comparison to a process wherein a conventional hydantoin racemase or no hydantoin racemase at all is used. An additional advantage of the hydantoin racemases according to the invention is that they have a broad substrate specificity, as a result of which they can be used in the preparation of many different enantiomerically enriched α-amino acids.

A hydantoin racemase that does not suffer from substrate inhibition is advantageously used in a method wherein an enantiomerically enriched hydantoin compound is contacted with said hydantoin racemase and wherein the concentration of the enantiomerically enriched hydantoin compound is above 5 mM, preferably above 7.5 or 10 mM, even more preferably above 15 or 20 and most preferred above 25 mM.

Alpha-amino acids with an amino acid rest group R, where R is as defined above are examples of enantiomerically enriched α-amino acids which can suitably be prepared in a process according to the invention wherein a hydantoin racemase according to the Invention Is used together with an enantioselective carbamoylase and a hydantoinase. Examples of α-amino acids are: alanine, valine, leucine, isoleucine, serine, threonine, methionine, cysteine, asparagine, glutamine, tyrosine, aspartic acid, glutamic acid, histidine, lysine, arginine, citrulline, phenylalanine, 3-fluorophenylalanine.

In such a process for the preparation of an enantiomerically enriched D- or L-α-amino acid use is preferably made of an enantioselective carbamoylase which has an enantioselectivity of at least 90%, more preferably an enantioselectivity of at least 95%, in particular at least 98%, most in particular an enanboselectivity of at least 99%. In the framework of the invention an enanboselectivity of the carbamoylase (for instance D-carbamoylase) of for instance 90% is understood to mean that the carbamoylase converts a racemic mixture of N-carbamoyl-D-α-amino acid and N-carbamoyl-L-α-amino acid into 90% of one of the enantiomers (for instance D-α-amino acid) and 10% of the other enantiomer (for instance L-α-amino acid) at an overall conversion of 50% of the racemic mixture of N-carbamoyl-D-α-amino acid and N-carbamoyl-L-α-amino acid.

The invention also relates to a process for the preparation of a D- or L-amino acid, from the corresponding N-carbamoyl-L-amino acid or N-carbamoyl-D-amino acid, or any mixture of N-carbamoyl-L-amino acid and N-carbamoyl-D-amino acid. In such a process a hydantoin racemase that does not suffer from substrate inhibition may be advantageously used together with a D- or L-carbamoylase and a hydantoinase, for instance in a single pot reaction.

In addition, the invention relates to the use of hydantoin racemases together with an enantioselective carbamoylase and a hydantoinase in the preparation of a D- or L-α-amino acid, respectively, from the corresponding L-α-amino acid or the corresponding D-α-amino acid, respectively, or any mixture of the corresponding D- and -L-α-amino acids. In an example of such a process wherein an L-α-amino acid is converted into a D-α-amino acid, the L-α-amino acid may first be converted chemically into the corresponding N-carbamoyl-L-α-amino acid, according to methods known in the art. The N-carbamoyl-L-α-amino acid may then be converted enzymatically into a D-α-amino acid in the presence of an enantioselective D-carbamoylase, a hydantoinase and a hydantoin racemase.

The temperature and the pH in a reaction in which a hydantoin racemase is involved are preferably chosen so as to achieve optimum stability and activity of the hydantoin racemase. If another enzyme is involved in the reaction, besides the hydantoin racemase, also the temperature and the pH are chosen so that the stability and the activity of both the hydantoin racemase and the activity, stability and, if desired enantioselectivity of the other enzyme are as good as possible. The conversion of N-carbamoyl-L-α-amino acid or N-carbamoyl-D-α-amino acid or of L- or D-hydantoin, respectively, into the corresponding D-α-amino acid or L-α-amino acid, respectively, in the presence of a hydantoin racemase according to the invention, a D- or L-carbamoylase, respectively, and a hydantoinase is preferably carried out at a pH between 5 and 10. In particular the conversion may be carried out at a pH between 6.0 and 7.5. The temperature of the conversion is preferably chosen between 0 and 80° C., in particular between 10 and 50° C., more in particular between 35 and 45° C.

The chemical preparation of N-carbamoyl-α-amino acid from the corresponding α-amino acid can for instance take place by contacting the α-amino acid with MOCN, where M represents alkali metal, preferably potassium or sodium. The temperature used is not critical: the reaction preferably takes place at temperatures between about −5 and 100° C., in particular at temperatures between 0 and 80° C.; the pH of the chemical reaction is preferably chosen between 8 and 11, more in particular between 9 and 10.

Preferably, the preparation of D-α-amino acid from the corresponding L-α-amino acid (or the other way round) via the corresponding N-carbamoyl-L-α-amino acid (or the corresponding N-carbamoyl-D-α-amino acid) is carried out in a single pot.

When use is made of hydantoin racemases in purified form or present in cell-free extract, an additive may be added to enhance the stability and/or activity of the hydantoin racemase (as for instance described in Watabe et al. 1992, J. Bact., pp. 7989–7995 and in Wiese et al. 2000, J. Bact, pp. 217–230). Examples of additives of this type are divalent sulphur containing compounds such as L-methionine, D-methionine, L-cysteine, N-carbamoyl-L-methionine, N-acetyl-D,L-methionine, 2-keto-4-(methylthio)butyric acid, D,L-2-hydroxy4(methylthio)butyric acid, L-methionine methylester, D,L-methionine hydroxamic acid, S-methyl-L-cysteine, D-biotine, β-mercaptoethanol, dithiotreitol (DTT), glutathione.

The invention is further explained below with reference to the following examples, without however being limited to these.

FIGURE LEGEND

FIG. 1: Relative initial activity of hydantoin racemases from *A. radiobacter*, *Pseudomonas* strain NS671 and *Arthrobacter aurescens* DSM 3747 versus initial L-5-methylmercaptoethylhydantoin concentration

EXAMPLES

General Procedures

Standard molecular biological techniques such as plasmid DNA isolation, agarose gel electrophoresis, enzymatic restriction modification of nucleic acids, *E. coli* transformation, etc., were carried out as described by Sambrook et al., 1989, "Molecular cloning: a laboratory manual", Cold Spring Harbor Laboratories, Cold Spring Harbor, N.Y., or according to the instructions for use provided by the various suppliers.

Synthetic oligodeoxynucleotides were purchased from Invitrogen (Groningen, Netherlands).

DNA sequence analysis was carried out by BaseClear (Leiden, Netherlands) using the chain termination method with colourant-labelled dideoxy terminators.

Protein concentrations In crude cell extracts were determined with the aid of Bradford reagent at 595 nm.

Example 1

Construction of pET-Hrac-S and pET-Hrac-L plasmids

An *Agrobacterium radiobacter* strain was precultured at 30° C. in LB medium consisting of 10 g/l trypton (Difco laboratories, Becton Dickinson microbiology systems, Sparks, USA), 5 g/l yeast extract (Difco) and 5 g/l sodium chloride. After overnight incubation the preculture was inoculated in fresh LB medium to an $OD_{600}$ of 0.2. This culture was further cultured at 30° C. and harvested at an $OD_{600}$ of 1.7.

The genomic DNA of this *A. radiobacter* culture was isolated by means of the method described by Qiagen (Qiagen genomic DNA handbook, 1998, Qiagen, Hilden, Germany).

The hydantoin racemase genes of *A. radiobacter* were cloned into expression vector pET101/D-TOPO (Invitrogen). The genes were cloned via a translation start (ATG) fusion and with the original stop codons, according to the method described by Invitrogen.

A fragment comprising 721 base pairs with the sequence of SEQ ID: NO.1, extended on the 5' side with the CACC sequence introduced by primer 1, was amplified by means of PCR from the chromosomal DNA of *A. radiobacter* with the following primers:

[Primer 1; SEQ ID: NO. 5]
5'-CACC<u>ATG</u>CATATTCGTCTGATCAACCCG-3'

(with the CACC sequence for directional TOPO cloning in bold type and the start codon underlined) and,

[Primer 2; SEQ ID: NO. 6]
5'-<u>TCA</u>GGCGACGAGCTTGGTTTC-3'

(with the stop codon underlined).

A fragment comprising 754 base pairs with the sequence of SEQ ID: NO. 3, extended on the 5' side with the CACC sequence introduced by primer 3, was amplified by means of PCR from the chromosomal DNA of *A. radiobacter* with the following forward primer:

[Primer 3; SEQ ID: NO. 7]
5'-CACC<u>ATG</u>GCAAATGAGCGTCCTGAAAG-3'

(with the CACC sequence for directional TOPO cloning in bold and the start codon underlined) and Primer 2 as the reverse primer.

The correct length of the amplified fragments was confirmed with agarose gel electrophoresis and the fragments were directly cloned into expression vector pET101/D-TOPO according to the supplier's protocol and transformed into *E. coli* TOP10 chemically competent cells (Invitrogen).

The transformants were selected on LB agar plates containing 100 mg/l carbenicillin. Plasmids with the correct insert (checked with the aid of bidirectional sequence determination) were called pET-Hrac-S and pET-Hrac-L, where Hrac-S stands for the insert with the sequence of SEQ ID: NO. 1 and Hrac-L for the insert with the sequence of SEQ ID: NO. 3. The plasmids were transformed into *E coli* TOP10. *E. coli* TOP10 (pET-Hrac-S) and *E. coli* TOP10 (pET-Hrac-L) were deposited under the Budapest treaty under No. 41131 and No. 41130, respectively, with the National Collections of Industrial, Food and Marine Bacteria (NCIMB, United Kingdom).

Example 2

Expression of the Hydantoin Racemases of *A. radiobacter* in *E. coli* BL21 Star (DE3)

Plasmid DNA of the pET-Hrac-S or pET-Hrac-L containing *E. coli* Top10 strains was isolated using the method described by Qiagen (plasmid mini-kit, protocol of October 2001) and subsequently transformed into chemically competent *E. coli* BL21 Star (DE3) cells (Invitrogen).

Single colonies of *E. coli* BL21 Star (DE3) (pET-Hrac-S) and *E. coli* BL21 Star (DE3) (pET-Hrac-L) were grown overnight at 28° C. in 25 ml LB medium with 100 mg/l carbenicillin to an $OD_{620nm}$ of 2.5. The entire cultures (25 ml) were inoculated into 250 ml fresh LB medium with 100 mg/l carbenicillin and grown further at 28° C. After 1 hour, at an $OD_{620nm}$ of 0.45, the cultures were induced by the addition of 1 mM (final concentration) of IPTG and grown further for 4.5 hours at 28° C., to an $OD_{620nm}$ of 1.7. The cells were subsequently harvested and washed with 100 mM potassium phosphate buffer, pH 7.0, optionally with 1 mM DTT, and then subjected to sonification, so that cell-free extract was obtained.

Portions of 30 mg of cells (wet weight) were frozen in at −20° C. for later use.

Example 3

Racemization Experiments Using the Overexpressed Hydantoin Racemase Genes from *A. radiobacter*

3.1 General Procedures

The 10 ml reaction mixes consisted of the final concentrations given below of D-5-benzylhydantoin, L-5-isopropylhydantoin or L-5-methylmercaptoethylhydantoin in 100 mM potassium phosphate buffer, pH 7.0. The reactions were started by adding the amounts given below of whole cells of *E. coli* BL21 Star (DE3) (pET-Hrac-S) or *E. coli* BL21 Star (DE3) (pET-Hrac-L) or cell-free extracts, with or without added dithiotreitol (DTT, 1 mM final concentration), and were incubated at room temperature.

The cell-free extracts were produced by resuspending 60 mg of cells in 1 ml 100 mM potassium phosphate buffer, pH 7.0, or 1 ml 100 mM potassium phosphate buffer, pH 7.0, with 1 mM DTT, followed by sonification.

Samples were taken (500 µl) and the reaction was stopped by the addition of 5 µl 85% phosphoric acid. The samples were analyzed by means of HPLC. D,L-5-isopropylhydantoin and D,L-5-benzylhydantoin were separated by means of a Chirobiotic T column (250 mm×4.6 mm, I.D. 5 µm) from Astec (Whippany, USA), D,L-5-methylmercaptoethylhydantoin was separated by means of a Chirobiotic T column (250 mm×4.6 mm, I.D. 5 µm) from Astec, combined with a Nucleosil 120-5 C18 column from Machery-Nagel (Duren, Germany). In all cases the eluent was 80% 15 mM ammonium acetate, pH 4.1, and 20% methanol. The eluent flow rate was 1 ml/min at a column temperature of 22° C. Detection took place by means of UV light at a wavelength of 220 nm. Under these conditions the retention times were 5.3 and 6.3 minutes for D- and L-5-isopropylhydantoin, respectively, 6.3 and 8.3 minutes for D- and L-5-benzylhydantoin, respectively, and 9.1 and 12.2 minutes for D- and L-5-methylmercaptoethylhydantoin, respectively.

3.2 Racemization of D-5 benzylhydantoin

In the same way as described in 3.1, 2 mM D-5-benzylhydantoin with an e.e. of 96% was incubated with cell-free extract (final protein concentration: 0.11 mg/ml). Cell-free extract of *E. coli* BL21 Star (DE3) (pET-Hrac-S) gave an e.e. of 52% after 4.5 hours. Cell-free extract of *E. coli* BL21 Star (DE3) (pET-Hrac-S) gave an e.e. of 80% after 4.5 hours.

The chemical blank gave an e.e. of 90% after 4.5 hours.

3.3 Racemization of L-5-isopropylhydantoin

In a set of reactions as described in 3.1, 40 mM L-5-isopropylhydantoin with an e.e. of 99% was incubated with whole cells (120 mg) and cell-free extract with DTT (final protein concentration: 0.44 mg/ml) of *E. coli* BL21 Star (DE3) (pET-Hrac-S) and *E. coli* BL21 Star (DE3) (pET-Hrac-L).

With whole cells and cell-free extract with DTT of *E. coli* BL21 Star (DE3) (pET-Hrac-S) an e.e. of 0% was achieved after 5 hours. With whole cells of *E. coli* BL21 Star (DE3) (pET-Hrac-L) an e.e. of 28% was achieved after 19 hours. With cell-free extract with DTT of *E. coli* BL21 Star (DE3) (pET-Hrac-L) an e.e. of 9% was achieved after 19 hours.

The chemical blank gave an e.e. of 98% after 19 hours.

3.4 Racemization of L-5-methylmercaptoethylhydantoin

In a set of reactions as described in 3.1 different concentrations of L-5-methylmercaptoethylhydantoin with an e.e. of 89% were incubated with whole cells of *E. coli* BL21 Star (DE3) (pET-Hrac-S) and *E. coli* BL21 Star (DE3) (pET-Hrac-L). The L-5-methylmercaptoethylhydantoin concentrations were 1, 5, 10, 50 and 80 mM. Initial reaction velocities were determined during the period of time in which the product concentration (D-5-methylmercaptoenthylhydantoin) increases linearly with time and are expressed in mM per hour. In FIG. 1 the initial activities are plotted versus the initial substrate concentrations.

As can be seen in FIG. 1, the Initial racemase activity of both *E. coli* BL21 Star (DE3) (pET-Hrac-S) and *E. coli* BL21 Star (DE3) (pET-Hrac-L) increases with an increasing initial substrate concentration, which means that the hydantoin racemases with SEQ ID: NO. 2 and NO. 4 do not exhibit substrate inhibition towards L-5-methylmercaptoethylhydantoin. The hydantoin racemases of Pseudomonas strain NS671 and *Arthrobacter aurescens* DSM 3747 on the other hand clearly show that the relative initial activity decreases at L-5-methylmercaptoethylhydantoin concentrations higher than 2.5 and 5 mM respectively. Therefore, it Is concluded that the cloned hydantoin racemases from *A. radiobacter* are not inhibited by L-5-methylmercaptoethylhydantoin. Km and Vmax values for L-5-methylmercaptoethylhydantoin were determined by plotting 1/V versus 1/S in a Lineweaver Burk plot. The cell free extract of *E. coli* BL21 Star (DE3) (pET-Hrac-S) has a Km of 1 mM and a Vmax of 0.4 mM/hour. The cell free extract of *E. coli* BL21 Star (DE3) (pET-Hrac-L) has a Km of 20 mM and a Vmax of 0.2 mM/hour.

The invention claimed is:

1. An isolated or recombinant polypeptide having hydantoin racemase activity, wherein the polypeptide comprises an amino acid sequence having at least 95% sequence identity to SEQ ID NO:4, or an enzymatically active subsequence thereof.

2. The isolated or recombinant polypeptide of claim 1, wherein the amino acid sequence has at least 97% sequence identity with SEQ ID NO:4, or an enzymatically active subsequence thereof.

3. The isolated or recombinant polypeptide of claim 2, wherein the amino acid sequence has at least 97% sequence identity with SEQ ID NO:4 or SEQ ID NO:2.

4. The isolated or recombinant polypeptide of claim 1, wherein the enzymatically active subsequence comprises SEQ ID NO:2.

5. The isolated or recombinant polypeptide of claim 1, wherein the amino acid sequence comprises SEQ ID NO:4.

6. The isolated or recombinant polypeptide of claim 1, wherein the amino acid sequence comprises SEQ ID NO:2.

7. A fusion protein comprising a first domain comprising a polypeptide as set forth in claim 1 and a second domain comprising a heterologous protein.

8. The fusion protein of claim 7, wherein the second domain comprising a heterologous protein comprises a secretion signal, a marker polypeptide or a polypeptide that facilitates purification of the protein.

9. An isolated or recombinant polypeptide having hydantoin racemase activity encoded by a nucleic acid which hybridizes under stringent conditions with SEQ ID NO:1 or SEQ ID NO:3, wherein the stringent conditions comprise two successive washing steps of 30 minutes each in 1=SSC, 0.1% SDS at 65° C.

10. The isolated or recombinant polypeptide of claim 1, wherein the polypeptide with hydantoin racemase activity does not suffer from substrate inhibition.

11. The isolated or recombinant polypeptide of claim 1, wherein the hydantoin racemase activity comprises racemization of D- or L-hydantoins.

12. The isolated or recombinant polypeptide of claim 11, wherein the D- or L-hydantoin comprises a D- or L-hydantoin as set forth in formula 1,

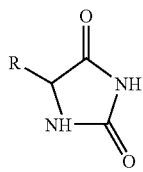

(1)

wherein the R group in formula 1 comprises an optionally substituted (hetero) alkyl group, optionally having 1 to 20 C-atoms, or an optionally substituted (hetero) aryl group, optionally having 1 to 20 C-atoms.

13. The isolated or recombinant polypeptide of claim 12, wherein a substituted (hetero) aryl group or a (hetero) alkyl group is selected from the group consisting of hydroxyl, alkoxy, mercapto, thioalkyl, alkyl, carboxyl, amino, nitro, halogens, carbamoyl, nitrile and acyl, and wherein an R group is selected from the group consisting of methyl, i-propyl, i-butyl, 2-methylthioethylene, 4-aminobutylene, hydroxymethylene, methoxymethylene, carboxymethylene, carboxyethylene, phenyl, p-hydroxyphenyl, m-hydroxyphenyl, o-hydroxyphenyl, p-chlorophenyl, m-chlorophenyl, 2,4-dichlorophenyl, p-methoxyphenyl, benzyl, p-hydroxybenzyl, 3,4-dihydroxybenzyl, 3,4-dimethoxybenzyl, benzyloxymethylene, 3, 4-methylenedioxybenzyl and indolylmethylene.

14. The isolated or recombinant polypeptide of claim 9, wherein the polypeptide with hydantoin racemase activity does not suffer from substrate inhibition.

15. The isolated or recombinant polypeptide of claim 9, wherein the hydantoin racemase activity comprises racemization of D- or L-hydantoins.

* * * * *